(12) United States Patent
Xu et al.

(10) Patent No.: US 10,287,289 B2
(45) Date of Patent: May 14, 2019

(54) PROCESS FOR PREPARING BETA 3 AGONISTS AND INTERMEDIATES

(71) Applicant: Merck Sharp & Dohme Corp., Rahway, NJ (US)

(72) Inventors: Feng Xu, Staten Island, NY (US); Zhuqing Liu, Edison, NJ (US); Richard Desmond, Readington, NJ (US); Jeonghan Park, Whippany, NJ (US); Alexei Kalinin, Morganville, NJ (US); Birgit Kosjek, Westfield, NJ (US); Hallena Strotman, Somerset, NJ (US); Hongmei Li, Westfield, NJ (US); Johannah Moncecchi, Waltham, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 87 days.

(21) Appl. No.: 14/776,366

(22) PCT Filed: Mar. 12, 2014

(86) PCT No.: PCT/US2014/023858
§ 371 (c)(1),
(2) Date: Sep. 14, 2015

(87) PCT Pub. No.: WO2014/150639
PCT Pub. Date: Sep. 25, 2014

(65) Prior Publication Data
US 2017/0145014 A1    May 25, 2017

Related U.S. Application Data

(60) Provisional application No. 61/791,247, filed on Mar. 15, 2013.

(51) Int. Cl.
| | | |
|---|---|---|
| *C12P 17/10* | (2006.01) | |
| *C12P 7/22* | (2006.01) | |
| *C12N 9/02* | (2006.01) | |
| *C12N 15/09* | (2006.01) | |
| *C07D 487/04* | (2006.01) | |
| *C07D 207/08* | (2006.01) | |
| *C07C 215/30* | (2006.01) | |
| *C07D 207/12* | (2006.01) | |

(52) U.S. Cl.
CPC .......... *C07D 487/04* (2013.01); *C07C 215/30* (2013.01); *C07D 207/08* (2013.01); *C07D 207/12* (2013.01); *C12P 17/10* (2013.01)

(58) Field of Classification Search
CPC .. C12N 9/0006; C12N 9/0008; C12N 9/1096; C12P 17/10; C12P 7/62; C12P 7/22; C12P 17/14
USPC ......... 435/135, 189, 121, 128, 25, 156, 106, 435/102
See application file for complete search history.

(56) References Cited

U.S. PATENT DOCUMENTS

| | | | |
|---|---|---|---|
| 8,247,415 | B2 | 8/2012 | Berger et al. |
| 8,399,480 | B2 | 3/2013 | Berger et al. |
| 8,653,260 | B2 | 2/2014 | Berger et al. |
| 2002/0028835 | A1 | 3/2002 | Hu et al. |
| 2007/0185136 | A1 | 8/2007 | Courtemanche et al. |
| 2011/0028481 | A1 | 2/2011 | Berger et al. |
| 2012/0202819 | A1 | 8/2012 | Edmondson et al. |
| 2012/0258963 | A1 | 10/2012 | Berger et al. |
| 2012/0322136 | A1 | 12/2012 | Mundorff et al. |
| 2013/0053403 | A1 | 2/2013 | Berger et al. |
| 2014/0242645 | A1 | 8/2014 | Chung et al. |
| 2015/0087832 | A1 | 3/2015 | Chung et al. |
| 2016/0176884 | A1 | 6/2016 | Chung et al. |

FOREIGN PATENT DOCUMENTS

| | | |
|---|---|---|
| WO | WO 03/072572 A1 | 9/2003 |
| WO | WO 2009/124166 A1 | 10/2009 |
| WO | WO 2009/124167 A1 | 10/2009 |
| WO | WO 2011/043942 A1 | 4/2011 |
| WO | WO2013062878 | 5/2013 |
| WO | WO2013062881 | 5/2013 |
| WO | WO2013074650 | 5/2013 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Dong et al., Convenient synthesis of homoproparglyglycine, Journal of Peptide Science, 2008, pp. 1148-1150, vol. 14.
International Search Report for PCT/US2014/023858, dated Jun. 6, 2014.
Xu, et al., Asymmetric Synthesis of cis-2,5-Disubstituted Pyrrolidine, the Core Scaffold of Beta-3-AR Agonists, Organic Letters, 2013, pp. 1342-1345, vol. 15 No. 6.
Huisman, et al., Current Opinion in Chemical Biology, Practical chiral alcohol manufacture using ketoreductases, 2009, pp. 1-8, 14.
Ebenezer, W.J. and Wight, P., "Ketones: α,β-Unsaturated Ketones," in *Comprehensive Organic Functional Group Transformations*, vol. 3, Katritzky, A.R., et al., eds., pp. 205-276, Elsevier Ltd., England (1995).

(Continued)

*Primary Examiner* — Robert B Mondesi
*Assistant Examiner* — Mohammad Y Meah

(57) ABSTRACT

The application is directed to efficient and economical processes as described in more detail below for the preparation of the beta 3 agonists of the formula of I-7 and intermediate compounds that can be used for making these agonists. The present disclosure relates to a process for making beta-3 agonists and intermediates using ketoreductase (KRED) biocatalyst enzymes and methods of using the biocatalysts.

20 Claims, 1 Drawing Sheet
Specification includes a Sequence Listing.

(56) References Cited

OTHER PUBLICATIONS

Extended European Search Report for EP Application No. 14768236.3, Munich, Germany, dated Nov. 28, 2016, 7 pages.
International Preliminary Report on Patentability and Written Opinion for International Application No. PCT/US2014/023858, The International Bureau of WIPO, Geneva, Switzerland, dated Sep. 15, 2015, 5 pages.
Koszelewski, D., et al., "Immobilization of ω-transaminases by encapsulation in a sol-gel/celite matrix," *Journal of Molecular Catalysis B: Enzymatic* 63:39-44, Elsevier B.V., Netherlands (2010).
Martin, A.R., et al., "Characterization of Free and Immobilized (S)-aminotransferase for Acetophenone Production," *Applied Microbiology and Biotechnology* 76(4):843-851, Springer International, Germany (2007).
Mateo, C., et al., "Epoxy Sepabeads: A Novel Epoxy Support for Stabilization of Industrial Enzymes via Very Intense Multipoint Covalent Attachment," *Biotechnology Progress* 18(3):629-634, American Chemical Society and American Institute of Chemical Engineers, United States (2002).
North, M., "Nitriles: General Methods and Aliphatic Nitriles," in *Comprehensive Organic Functional Group Transformations*, vol. 3, Katritzky, A.R., et al., eds., pp. 611-640, Elsevier Ltd., England (1995).
Parkes, K.E.B. and Richardson, S.K., "Ketones: Dialkyl Ketones," in *Comprehensive Organic Functional Group Transformations*, vol. 3, Katritzky, A.R., et al., eds., pp. 111-204, Elsevier Ltd., England (1995).
Sonogashira, K., "Palladium-Catalyzed Alkynylation: Sonogashira Alkyne Synthesis," in *Handbook of Organopalladium Chemistry for Organic Synthesis*, Negishi, E-I., ed., pp. 493-529, John Wiley & Sons, Inc., United States (2002).

Truppo, M.D. and Hughes, G., "Development of an Improved Immobilized CAL-B for the Enzymatic Resolution of a Key Intermediate to Odanacatib," *Organic Process Research & Development* 15(5):1033-1035, American Chemical Society, United States (2011).
Yi, S.S., et al., "Covalent Immobilization of ω-transaminase from *Vibrio fluvialis* JS17 on chitosan beads," *Process Biochemistry* 42(5):895-898, Elsevier Ltd., England (2007).
Xu, F., et al., "Asymmetric Synthesis of cis-2,5-Disubstituted Pyrrolidine, the Core Scaffold of $\beta_3$-AR Agonists," *Organic Letters* 15(6):1342-1345, American Chemical Society, United States (2013).
International Preliminary Report on Patentability and Written Opinion for International Application No. PCT/US2009/039249, The International Bureau of WIPO, Geneva, Switzerland, dated Oct. 5, 2010, 6 pages.
International Preliminary Report on Patentability and Written Opinion for International Application No. PCT/US2009/039253 The International Bureau of WIPO, Geneva, Switzerland, dated Oct. 5, 2010, 5 pages.
International Preliminary Report on Patentability and Written Opinion for International Application No. PCT/US2012/061252, The International Bureau of WIPO, Geneva, Switzerland, dated Apr. 29, 2014, 4 pages.
International Search Report for International Application No. PCT/US2009/039249, European Patent Office, Netherlands, dated Aug. 31, 2009, 4 pages.
International Search Report for International Application No. PCT/US2009/039253, European Patent Office, Netherlands, dated Jun. 17, 2009, 3 pages.
International Search Report for International Application No. PCT/US2012/061252, European Patent Office, Netherlands, dated Jan. 18, 2013, 2 pages.

\* cited by examiner

PROCESS FOR PREPARING BETA 3 AGONISTS AND INTERMEDIATES

CROSS REFERENCE TO RELATED APPLICATIONS

This application is a U.S. National Phase application under 35 U.S.C. § 371 of PCT Application No. PCT/US2014/023858, filed Mar. 12, 2014, which claims priority under 35 U.S.C. § 119(e) from U.S. Provisional Application Ser. No. 61/791,247, filed on Mar. 15, 2013.

TECHNICAL FIELD

The present disclosure relates to a process for making beta-3 agonists and intermediates using ketoreductase (KRED) biocatalyst enzymes and methods of using the biocatalysts.

REFERENCE TO SEQUENCE LISTING, TABLE OR COMPUTER PROGRAM

The official copy of the Sequence Listing is submitted concurrently with the specification as an ASCII formatted text file via EFS-Web, with a file name "23146-SeqList.txt", a creation date of Mar. 7, 2014, and a size of 2.68 kb. The Sequence Listing filed via EFS-Web is part of the specification and is incorporated in its entirety by reference herein.

BACKGROUND OF THE INVENTION

The application is directed to efficient and economical processes, as described in more detail below, for the preparation of the beta 3 agonists of formula I-7 and intermediate compounds that can be used for making these agonists.

SUMMARY OF THE INVENTION

Figure 1:
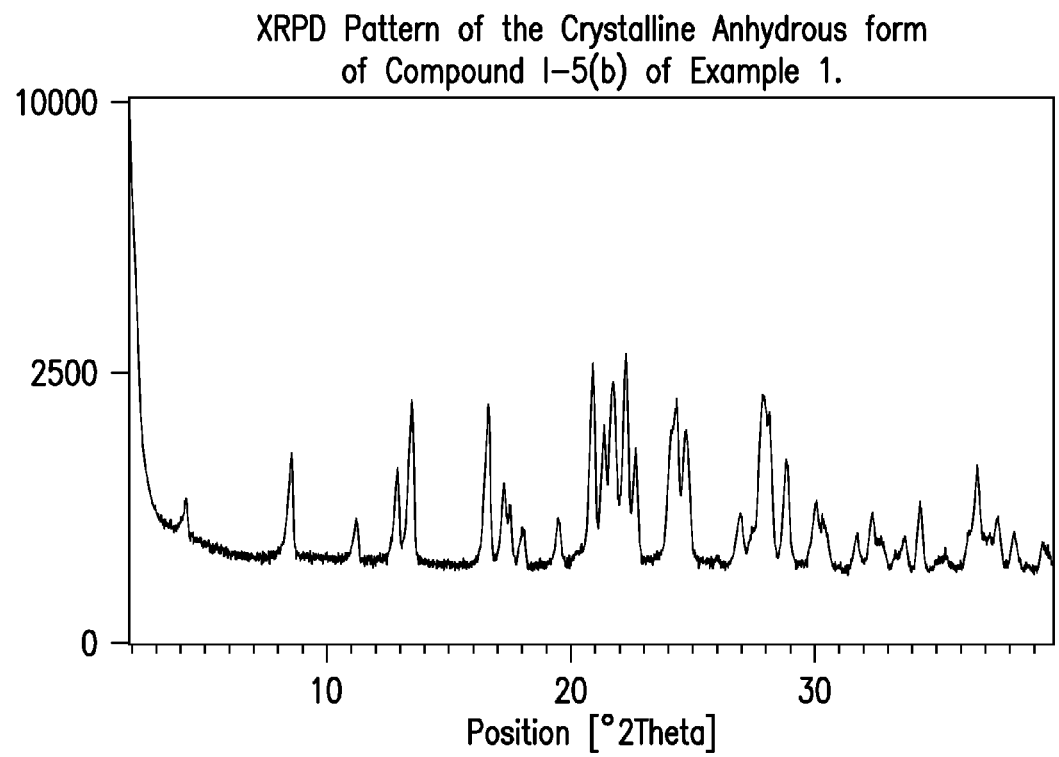
FIG. 1 is a powder X-ray diffraction pattern of the crystalline salt form of Compound I-5(b) of Example 1.
Figure 2:
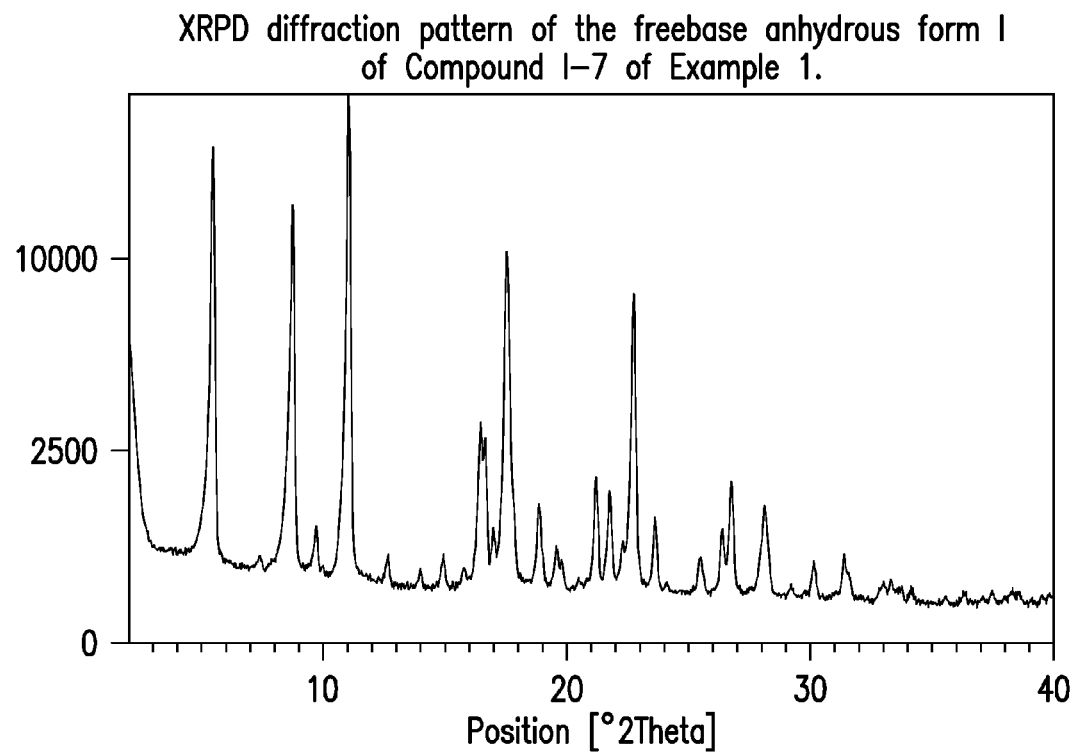
FIG. 2 is a powder X-ray diffraction pattern of the freebase anhydrous form I of Compound I-7 of Example 1.

This application is directed to a multiple-step synthetic process for making a compound of formula I-7 and its intermediates. A KRED enzyme is used in the multiple-step process.

DESCRIPTION OF THE INVENTION

Described herein is a process of making compound I-6, a key intermediate for making beta-3 agonists, from compound I-3.

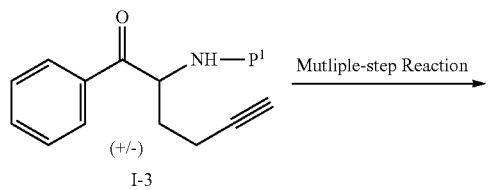

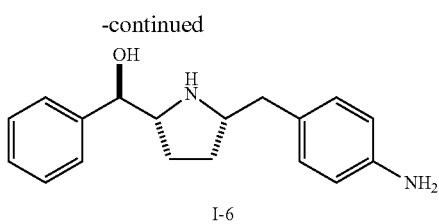

In the first embodiment, the multiple-step reactions from compound I-3 to compound I-6 comprise the following steps:

(a-2) reducing compound I-3:

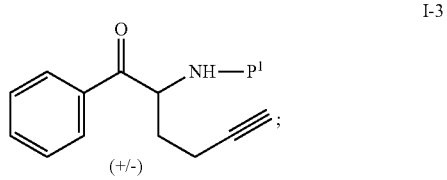

in the presence of a KRED enzyme to produce compound I-4:

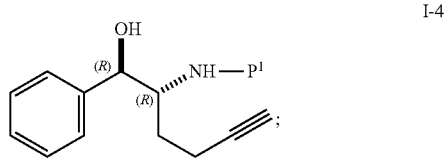

(b-2) coupling compound I-4 with compound A-1 in the presence of Catalyst D to produce compound I-5(a)

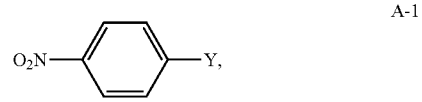

followed by deprotecting in situ with an acid to produce compound I-5(b) as a salt:

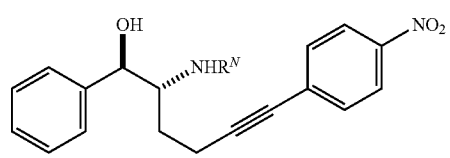

I-5(a), where $R^N = P^1$ or I-5(b) where, $R^N = H$;

(c-2) cyclizing and reducing compound I-5(b) in the presence of Catalyst E to produce compound I-6 via I-6-1:

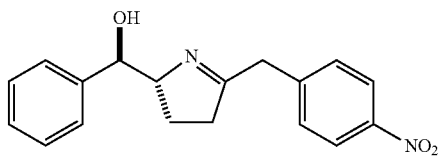

I-6-1

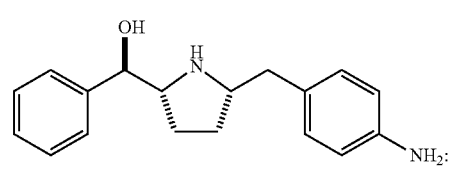

I-6 wherein $P^1$ is selected from the group consisting of Ac, Bn, Boc, Bz, Cbz, DMPM, FMOC, Ns, Moz, and Ts; and Y is selected from Cl, I, Br, and OTf; and R is selected from the group consisting of H, TMS, TES, TBDMS, TIPS and TBDPS;

and $R^N$ is $P^1$ or H.

Also, described herein is a process of making compound I-7 from compound I-3 through multiple step reactions:

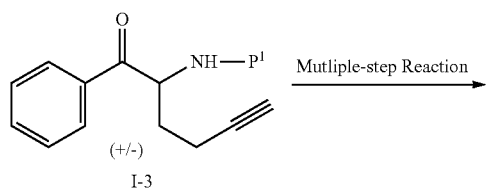

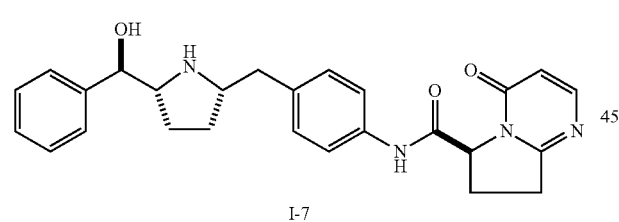

I-7

In the second embodiment, the multiple-step reactions from compound I-3 to compound I-7 comprise the following steps:

(a-2) reducing compound I-3:

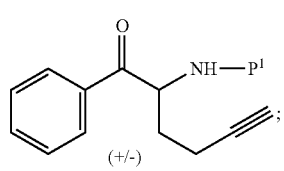

I-3 in the presence of a KRED enzyme to produce compound I-4:

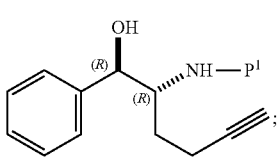

I-4

(b-2) coupling compound I-4 with compound A-1 in the presence of Catalyst D to produce compound I-5(a)

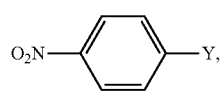

A-1 followed by deprotecting in situ with an acid to produce compound I-5(b) as a salt:

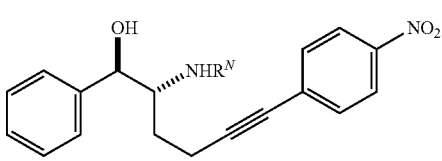

I-5(a), where $R^N$=$P^1$ or I-5(b) where, $R^N$=H;

(c-2) cyclizing and reducing compound I-5(b) in the presence of Catalyst E to produce compound I-6 via I-6-1:

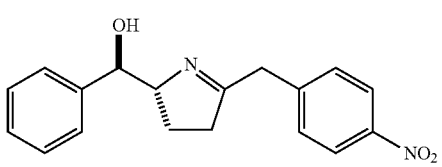

I-6-1

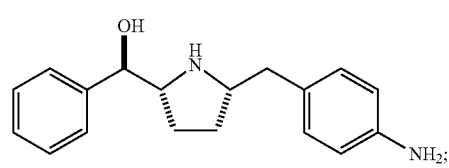

I-6

(d-2) coupling compound I-6 with compound A-2:

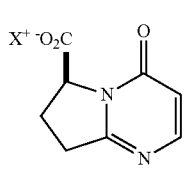

A-2 in the presence of a coupling agent and optionally including a base to produce compound I-7;

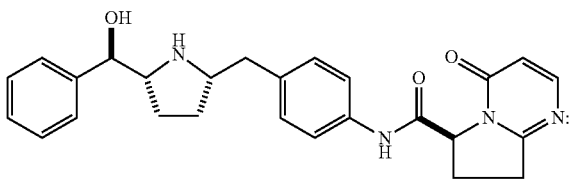

wherein P¹ is selected from the group consisting of Ac, Bn, Boc, Bz, Cbz, DMPM, FMOC, Ns, Moz, and Ts; and X is selected from Na, Li, and K;

Y is selected from Cl, I, Br, and OTf; and

R is selected from the group consisting of H, TMS, TES, TBDMS, TIPS and TBDPS;

and $R^N$ is P¹ or H.

Also described herein is a process of making compound I-6, a key intermediate for making beta-3 agonists, from compound I-1.

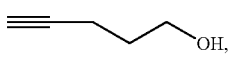

In the third embodiment, the multiple-step reactions from compound I-1 to compound I-6 comprise the following steps:

(a-1) reacting compound I-1:

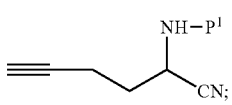

in the presence of a solvent, an oxidizing agent, and Catalyst A to form an aldehyde in situ, followed by a condensation in the presence of X—CN and ammonium salt and a protective reagent, $P^1_2O$ or P¹Cl, to produce compound I-2:

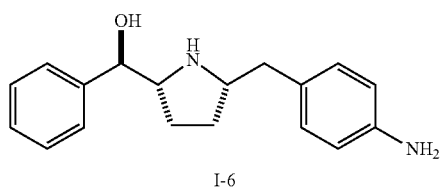

(b-1) reacting compound I-2 in the presence of phenyl Grignard reagent to produce compound I-3:

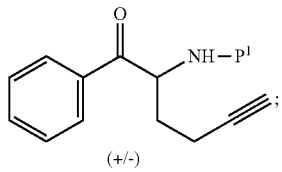

(c-1) reducing compound I-3 in the presence of a KRED enzyme to produce compound I-4:

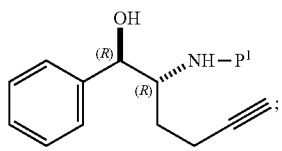

(d-1) coupling compound I-4 with compound A-1 in the presence of Catalyst D to produce compound I-5(a)

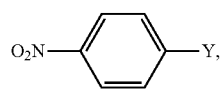

followed by deprotecting in situ with an acid to produce compound I-5(b) as a salt:

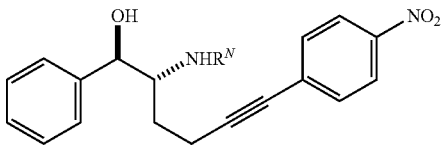

I-5(a), where $R^N$=P¹ or I-5(b) where, $R^N$=H;

(e-1) cyclizing and reducing compound I-5(b) in the presence of Catalyst E to produce compound I-6 via I-6-1:

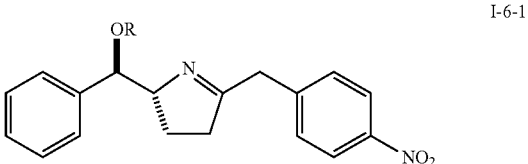

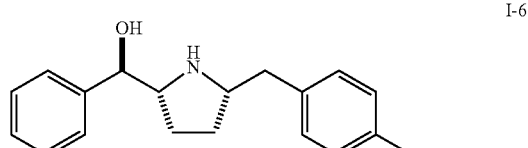

wherein P¹ is selected from the group consisting of Ac, Bn, Boc, Bz, Cbz, DMPM, FMOC, Ns, Moz, and Ts; and X is selected from Na, Li, and K;

Y is selected from Cl, I, Br, and OTf; and

R is selected from the group consisting of H, TMS, TES, TBDMS, TIPS and TBDPS;

And $R^N$ is $P^1$ or H.

In one embodiment, the solvent in step (a-1), as set forth in the first above embodiment, is selected from the group consisting of THF, MTBE, $CH_2Cl_2$, MeCN, EtOAc, i-PrOAc, Me-THF, hexane, heptane, DMAc, DMF, methyl cyclopentyl ether, toluene and a mixture comprising two or more of the foregoing solvents. In a preferred embodiment the solvent used in step (a-1) is MeCN. In another embodiment, the oxidizing agent is selected from the group consisting of NaOCl, $NaClO_2$, $PhI(OAc)_2$, hydrogen peroxide, pyridine sulfur trioxide/$Et_3N$/DMSO and various Moffatt variants (see Ketones: Dialkyl Ketones. Parkes, Kevin E. B. and Richardson, Stewart K. in Comprehensive Organic Functional Group Transformations, Volume 3, 1995, Pages 111-204, Editor(s): Katrizky, Alan R.; Meth-Cohn, Otto; Rees, Charles Wayne, Elsevier, Oxford, UK), PCC, DCC, Swern oxidation (oxalic chloride-DMSO-trialkyl amine; see Ketones: Dialkyl Ketones. Parkes, Kevin E. B. and Richardson, Stewart K. in Comprehensive Organic Functional Group Transformations, Volume 3, 1995, Pages 111-204, Editor(s): Katrizky, Alan R.; Meth-Cohn, Otto; Rees, Charles Wayne, Elsevier, Oxford, UK) or its variants, TPAP/NMO.

In another embodiment, the oxidation of step (a-1), as set forth in the first above embodiment, is carried out using Catalyst A which is TEMPO and its variants including, but not limited to TEMPO/bleach/NaBr, TEMPO/trichloroisocyanuric acid, TEMPO/NCS/TBACl, TEMPO/NCS. In another embodiment, Catalyst A is TEMPO or a TEMPO analogue in the presence or absence of a bromide salt. In another embodiment, the preferred Tempo oxidation combination is TEMPO-bleach-bromide salt and TEMPO-PhI$(OAc)_2$; In a further embodiment a combination of TEMPO-PhI$(OAc)_2$ with additional additives such as HOAc and water is used. In another embodiment, the protective group is Boc. In a further embodiment, the Boc protection with $(Boc)_2O$ is carried out at a temperature of about 35 to about 45° C. using EtOAc or i-PrOAc.

Alternatively, compound I-2 can be prepared via hydrogensulfite adduct.

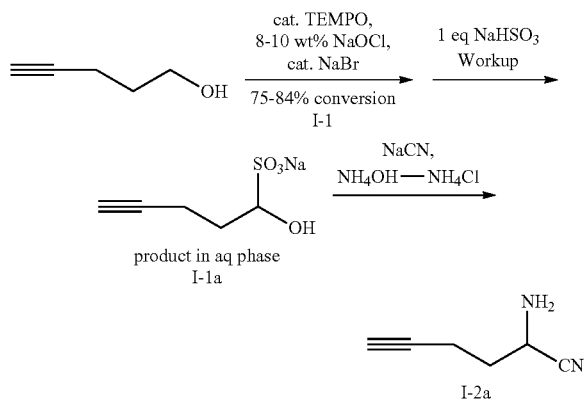

In one embodiment, the reaction in step (b-1), as set forth in the first above embodiment, is carried out at a temperature of about −20° C. to about 40° C. In another embodiment, the reaction in step (b-1), as set forth in the first above embodiment, is carried out at a temperature of about −15° C. to about 5° C.

In another embodiment, the reaction in step (b-1), as set forth in the first above embodiment, is carried out in the presence of a solvent selected from the group consisting of THF, MTBE, $CH_2C_2$, Me-THF, hexane, heptane, methyl cyclopentyl ether, toluene and a mixture comprising two or more of the foregoing solvents.

In another embodiment, the Grignard reagent in step (b-1), as set forth in the first above embodiment, is PhMgBr or PhMgCl.

In one embodiment, the dynamic kinetic reduction in the presence of KRED enzyme in step (c-1 or a2), as set forth in the first, second or third embodiments above, is a polypeptide comprising the amino acid sequence set forth in SEQ ID NO. 1 or an active fragment thereof. In another embodiment, the reaction in step (c-1 or a-2), as set forth in the first, second or third embodiments above, is carried out in a pH range of greater than about pH 8 and higher. In a further embodiment, the reaction in step (c-1 or a-2), as set forth in the first, second or third embodiments above, is carried out at a pH of about 10±0.5. In another embodiment, the reaction of step (c-1 or a-2), as set forth in the first, second or third embodiments above, is carried out at a temperature range of about 30° C. to about 50° C. In a further embodiment, the reaction of step (c-1 or a-2), as set forth in the first, second or third embodiments above, is carried out at a temperature range of about 43° C. to about 47° C.

The Sonogoshira coupling reaction carried out in step (d-1 or b-2), as set forth in the first, second or third embodiments above, is the coupling of a terminal alkyne with an aryl or vinyl halide and is performed with a palladium catalyst, a copper(I) cocatalyst, or an amine base (see Sonogoshira, K. In Handbook of Organopalladium Chemistry for Organic Synthesis; Negishi, E., Ed.; Wiley-Interscience: New York, 2002; pp 493-529.). In one embodiment, Catalyst D used in the Sonogoshira reaction in step (d-1 or b-2) is selected from the group consisting of $Pd(PPh_3)_4$, $PdCl_2$, $(PPh_3)_2PdCl_2$, $Pd(dppe)Cl$, $Pd(dppp)Cl_2$, $Pd(dppf)Cl_2$, and $Pd(OAc)_2/Ph_3P$ or other ligands, in the presence or absence of catalytic amount of material selected from CuI, CuBr, and CuCl. In a further embodiment, the catalyst combination is $(PPh_3)_2PdCl_2$ and CuI. In another embodiment, the reaction in step (d-1 or b-2), as set forth in the first, second or third embodiments above, is carried out in the presence of a solvent selected from THF, IPA, MeOH, EtOH, n-PrOH, NMP, DMF, DMAc, MTBE, $CH_2Cl_2$, MeCN, Me-THF, methyl cyclopentyl ether, and toluene, and a mixture comprising two or more of the foregoing solvents. In another embodiment, the reaction in step (d-1 or b-2), as set forth in the first, second or third embodiments above, is carried out in the presence of a solvent made up of a mixture of THF and IPA. In one embodiment, the acid used in the reaction in step (d-1 or b-2), as set forth in the first, second or third embodiments above, to removal carbamate protecting group is selected from HCl, HBr, TFA, $MeSO_3H$, $H_2SO_4$, p-toluenesulfonic acid, phenylsulfonic acid, camphorsulfonic acid, bromo-camphorsulfonic acid, and other sulfonic acids such as $RSO_3H$, wherein R is $C_{1-6}$ alkyl, aryl or substituted aryl. In another embodiment, the acid used in the reaction in step (d-1 or b-2), as set forth in the first, second or third embodiments above, is HCl. In a further embodiment, the reaction product in step (d-1 or b-2), as set forth in the first, second or third embodiments above, is isolated as a solid HCl salt.

In one embodiment, compound I-5(b) acidic salt reacts in step (e-1 or c-2), as set forth in the first, second or third embodiments above, with a base selected from, but not limited to, Et₃N, i-Pr₂NEt, i-Pr₂NH, pyridine, lutidine, N-methyl morphine, t-BuOK, t-BuONa, t-BuOLi, NaH, NaHMDS, LiHMDS, and KHMDS to produce compound I-6-1 through an intramolecular cyclization reaction:

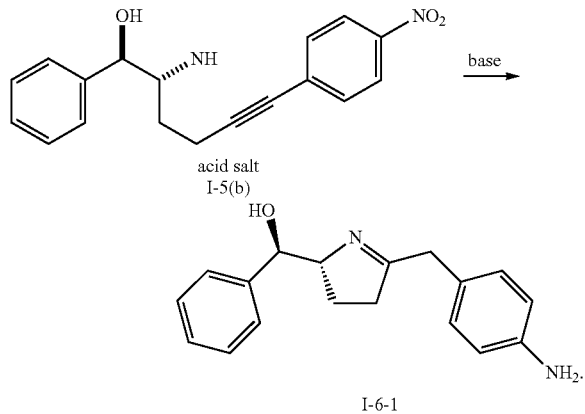

In one embodiment, the base is Et₃N, i-Pr₂NEt, or i-Pr₂NH. In another embodiment, the base is i-Pr₂NEt.

In one embodiment, compound I-6-1 is reduced to compound I-6 in the presence of a catalyst:

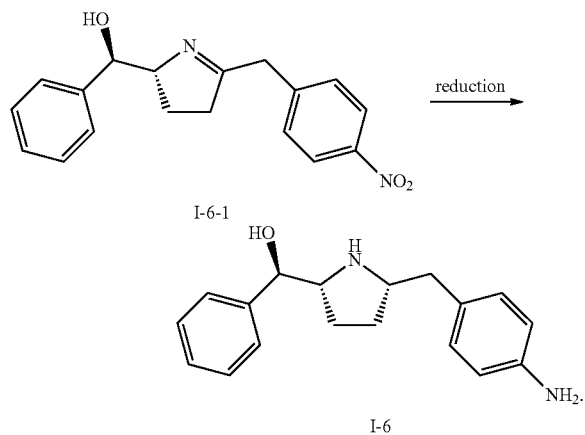

The reaction conditions for the conversion from I-6-1 to I-6 can be controlled using a cis-selective hydrogenation process. In one embodiment, the cis-selective hydrogenation of step (e-1 or c-2), as set forth in the first, second or third embodiments above, is carried out in the presence of Catalyst E selected from the group consisting of Pt on alumina, Pd on alumina, Rh on alumina, Pd/C, Pd(OH)₂—C, Pt on alumina-V on carbon or vanadate, Raney Ni, Rh/C, Rh/Al, Pt/C, Ru/C and PtO₂. In another embodiment, Catalyst E is Pt on alumina.

In another embodiment, the cis-selective hydrogenation from I-6-1 to I-6 in step (e-1 or c-2) is carried out in the presence of a hydroxyl protecting reagent, which protects the hydroxy group in situ and therefore improves the diastereoselectivity. Protecting reagents can be selected from the TMSCl, HMDS, TESCl, TIPSCl, and TBDMSCl. In another embodiment, the protecting reagent is TMSCl.

In one embodiment, the hydrogenation reaction of step (e-1 or c-2), as set forth in the first, second or third embodiments above, is carried out at about 10° C. to about 70° C. In another embodiment, the hydrogenation reaction of step (e-1 or c-2), as set forth in the first, second or third embodiments above, is carried out at about 20° C. to about 50° C. In a further embodiment, the hydrogenation reaction of step (e-1 or c-2), as set forth in the first, second or third embodiments above, is carried out stagewise at about 20° C. and then at about 50° C.

In another embodiment, the reduction reaction of step (e-1 or c-2), as set forth in the first, second or third embodiments above, is carried out in the presence of hydrogen gas. In another embodiment, the pressure of the hydrogen gas ranges from about 15 to about 400 psi. In a further embodiment, the pressure of the hydrogen gas ranges from about 50 to about 100 psi.

The reaction between I-6 and A-2 can be carried out in the presence of a coupling reagent. Suitable coupling reagents include, but are not limited to, CDI, DCC, EDC, EDC methiodide, T3P, HATU, HBTU and mix-anhydrides. In another embodiment, the coupling agent is DCC, EDC, or EDC methiodide. In a further embodiment, the coupling reagent is EDC.

The reaction between I-6 and A-2 can be carried out in the presence of a solvent while the substrate is treated with an acid such as HCl, MeSO₃H, H₂SO₄ to selectively protect the secondary pyrrolidine amine. Suitable solvents include, but are not limited to, both aqueous and non-aqueous solvents such as MeOH, EtOH, isopropyl alcohol (IPA), n-PrOH, MeCN, DMF, DMAc, NMP, THF, EtOAc, IPAc, or toluene.

A promoter can be used in the reaction between I-6 and A-2. Suitable promoters include, but are not limited to, HOBT and HOPO.

Suitable pH values for the reaction between I-6 and A-2 can be about 2.5 to about 5.0, or more specifically, about 3.0 to about 4.0, or even more specifically, about 3.0 to about 3.5. The pH can be adjusted to the desired ranges using an acid such as HCl, HBr, HI, HNO₃, H₂SO₄, H₃PO₄, TFA and MeSO₃H. In one embodiment, the pH is about 3.0 to about 3.7. In another embodiment, the pH is about 3.3 to about 3.5.

In one embodiment, the reaction in step (d-2), as set forth in the second or third embodiments above, is carried out in the presence of a base. In a further embodiment, the reaction in step (d-2), as set forth in the second or third embodiments above, is carried out in the presence pyridine or pyridine salt. Pyridine salt includes, but not limited to the corresponding HCl salt, H₂SO₄ salt, H₃PO₄ salt, HBr salt, HI salt, HNO₃ salt, or MeSO₃H salt.

In the first, second or third embodiments listed above, the KRED enzyme comprises a polypeptide sequence set forth in SEQ ID NO.1 or an active fragment thereof.

In the first, second or third embodiments listed above, a cofactor recycling system is also present in addition to a KRED enzyme. Suitable cofactor recycling systems include, but are not limited to, a KRED enzyme such as polypeptide of SEQ ID NO.1 and a glucose deydrogenase enzyme.

In the first, second or third embodiments listed above, a KRED enzyme comprising a polypeptide sequence set forth in SEQ ID NO.1 or an active fragment thereof and a cofactor recycling system are present in the reduction from I-3 to I-4.

In the first, second or third embodiments listed above, a cofactor molecule which can donate a hydride is also present in addition to a KRED enzyme. In one embodiment, the cofactor is selected from the group consisting of NADH and NADPH.

In the first, second or third embodiments listed above, a co-substrate molecule which can provide a hydride for the recycling of a cofactor molecule is also present in addition to a KRED enzyme. In one embodiment, the co-substrate is selected from the group of secondary alcohols including but not limited to 2-propanol, 2-butanol, 2-pentanol, 2-hexanol, 2-heptanol, and 2-octanol.

In the first, second or third embodiments listed above, the enzymatic reduction of I-3 to I-4 is carried out in a solvent. Suitable solvents can be selected from the group consisting of 2-propanol, sec-butanol, iso-butanol, 2-pentanol, 2-hexanol, 2-heptanol, 2-octanol, DMSO, DMF, DMAc, and NMP, and combinations thereof. In one embodiment, the solvent is 2-propanol.

In the first, second or third embodiments listed above, a suitable temperature for the dynamic kinetic resolution (DKR) reduction from I-3 to I-4 ranges from about 0° C. to about 60° C., or more specifically, from about 30° C. to about 50° C., or even more specifically, from about 43° C. to about 47° C. In one embodiment, the temperature is about 45° C.

In the first, second or third embodiments listed above, a KRED enzyme is coupled with a cofactor recycling system and an NADPH cofactor is used to reduce compound I-3 to obtain compound I-4. Suitable reaction conditions for the KRED-catalyzed reduction of I-3 to I-4 are provided below and in the Examples.

In the first, second or third embodiments listed above, the KRED enzyme or active fragment thereof can be immobilized on a solid support. In some embodiments, the KRED enzyme or active fragment thereof having ketoreductase activity of the present disclosure can be immobilized on a solid support such that they retain their improved activity, stereoselectivity, and/or other improved properties relative to the reference polypeptide of SEQ ID NO: 1 or active fragment thereof. In such embodiments, the immobilized polypeptides can facilitate the biocatalytic conversion of the substrate of compound I-3 or structural analogs thereof to the product of compound I-4 or corresponding structural analogs (e.g., as shown in the process of Scheme 1 described herein), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the KRED enzyme or active fragment thereof of the present disclosure can be carried out using the same KRED enzyme or active fragment thereof bound or immobilized on a solid support.

Methods of enzyme immobilization are well-known in the art. The KRED enzyme can be bound non-covalently or covalently. Various methods for conjugation and immobilization of enzymes to solid supports (e.g., resins, membranes, beads, glass, etc.) are well known in the art and described in e.g.: Yi et al., "Covalent immobilization of ω-transaminase from Vibrio fluvialis JS17 on chitosan beads," Process Biochemistry 42(5): 895-898 (May 2007); Martin et al., "Characterization of free and immobilized (S)-aminotransferase for acetophenone production," Applied Microbiology and Biotechnology 76(4): 843-851 (September 2007); Koszelewski et al., "Immobilization of ω-transaminases by encapsulation in a sol-gel/celite matrix," Journal of Molecular Catalysis B: Enzymatic, 63: 39-44 (April 2010); Truppo et al., "Development of an Improved Immobilized CAL-B for the Enzymatic Resolution of a Key Intermediate to Odanacatib," Organic Process Research & Development, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," Biotechnology Progress 18(3):629-34 (2002); and Bioconjugation Protocols: Strategies and Methods, In Methods in Molecular Biology, C. M. Niemeyer ed., Humana Press (2004); the disclosures of each which are incorporated by reference herein.

Solid supports useful for immobilizing the KRED enzyme of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the KRED enzyme of the present disclosure include, but are not limited to, chitosan beads, Eupergit® C, and SEPABEADS® (Mitsubishi Chemical Company), including the following different types of SEPABEAD®: HP2MG; EC-EP, EC-HFA/S; EXA252, EXE119 and EXE120. In some embodiments, the solid support can be a bead or resin comprising carbonate.

KRED enzymes belonging to class of oxidoreductases are useful for the synthesis of optically active alcohols from the corresponding pro-stereoisomeric ketone substrates by stereospecific reduction of corresponding racemic aldehyde and ketone substrates. Isolated ketoreductases require the presence of a nicotinamide cofactor. Hydrogen and two electrons are transferred from the reduced nicotinamide cofactor (NADH or NADPH) to the carbonyl group of the substrate to effect a reduction to the chiral alcohol.

In the first, second or third embodiments listed above, compound I-7 is obtained in the form of a crystalline anhydrous free base. In the first, second or third embodiments listed above, compound I-7 is obtained in the form of a crystalline free base hemihydrate.

As used herein, the term "alkyl" means both branched- and straight-chain saturated aliphatic hydrocarbon groups having the specified number of carbon atoms. For example, $C_{1-6}$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl and isohexyl.

As used herein, the term "aryl" refers to an aromatic carbocycle. For example, aryl includes, but is not limited to, phenyl and naphthalyl.

Throughout the application, the following terms have the indicated meanings unless noted otherwise:

| Term | Meaning |
| --- | --- |
| Ac | Acyl ($CH_3C(O)$—) |
| Bn | Benzyl |
| BOC (Boc) | t-Butyloxycarbonyl |
| $(Boc)_2O$ | Di-tert-butyl dicarbonate |
| t-BuOK | Potassium tert-butoxide |
| t-BuOLi | Lithium tert-butoxide |
| t-BuONa | Sodium tert-butoxide |
| Bz | Benzoyl |
| Cbz | Carbobenzyloxy |
| CDI | 1,1'Carbonyldiimidazole |
| DCC | N,N'-Dicyclohexycarbodiimide |
| DCM | Dichloromethane |
| DKR | Dynamic kinetic resolution |
| DMAc | N,N-dimethylacetamide |
| DMAP | 4-Dimethylaminopyridine |
| DMF | N,N-dimethylformamide |
| DMPM | 3,4-Dimethoxybenzyl |
| DMSO | Dimethyl sulfoxide |
| DABCO | 1,4-diazabicyclo[2.2.2]octane |
| dr (Dr) | diastereomer ratio |
| EDC | 1-Ethyl-3-(3-dimethylaminopropyl) carbodiimide |

| Term | Meaning |
| --- | --- |
| ee | enantiomeric excess |
| Et | Ethyl |
| EtOAc | Ethyl acetate |
| FMOC | 9-Fluorenylmethyloxycarbonyl |
| HATU | O-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate) |
| HMDS | Hexamethyldisilazane |
| HOBT | 1-Hydroxy-1H-benzotriazole |
| HOPO | 2-Hydroxypyridine-N-oxide |
| Immobead ™ 150A | an apolar enzyme carrier bead of macroporous acrylic polymer |
| IPA | Isopropyl Alcohol |
| KHMDS | Potassium bis(trimethylsilyl)amide |
| KRED | Ketoreductase |
| LC/MS or LC-MASS | Liquid chromatography mass spectrum |
| LCAP | Liquid Chromatography Area Percent |
| Me | Methyl |
| Moz or MeOZ | p-Methoxybenzyl carbonyl |
| MTBE | Methyl tert-butyl ether |
| NaHMDS | Sodium hexamethyldisilazide |
| NADP | Nicotinamide adenine dinucleotide phosphate sodium salt |
| NMP | N-Methyl-2-pyrrolidone |
| Ns | 4-Nitrobenzene sulfonyl |
| OTf | Triflate |
| PCC | Pyridinium chlorochromate |
| 5% Pd/Al$_2$O$_3$ | Palladium, 5 weight percent on aluminum oxide |
| 5% Pd/C | Palladium, 5 weight percent on activated carbon |
| 10% Pd/C | Palladium, 10 weight percent on activated carbon |
| PdCl$_2$ | Palladium (II) chloride |
| (PPh$_3$)$_2$PdCl$_2$ | Bis(triphenylphosphine)palladium(II) dichloride |
| Pd(dppe)Cl | 1,2-bis(diphenylphosphino)ethane chloropalladium |
| Pd(dppp)Cl$_2$ | 1,3-bis (diphenylphosphino)propane dichloropalladium(II) |
| Pd(dppf)Cl$_2$ | 1,1'-bis(diphenylphosphino)ferrocene dichloropalladium(II) |
| PhI(OAc)$_2$ | Iodobenzene diacetate |
| PhMgBr | Phenyl Magnesium Bromide |
| (PPh$_3$)$_2$PdCl$_2$ | Triphenyl phospate Palladium Chloride |
| 5% Pt/Al$_2$O$_3$ | Platinum, 5 weight percent on aluminum oxide |
| Ph | Phenyl |
| i-PrOAc | Isopropyl acetate |
| PrOH | Propyl alcohol |
| i-Pr$_2$NEt | Diisopropylethylamine (DIPEA) |
| i-Pr$_2$NH | Diisopropylamine |
| 5% Rh/Al$_2$O$_3$ | Rhodium, 5 weight percent on aluminum oxide |
| T3P | Propane Phosphonic Acid Anhydride |
| TBACl | Tetrabutylammonium chloride |
| TBDMS | t-Butyldimethylsilyl |
| TBDPS | tert-Butyldiphenylsilyl ether |
| TBDMSCl | Tert-Butyldimethylsilyl chloride |
| TEA or Et$_3$N | Triethylamine |
| TEMPO | 1-Oxyl-2,2,6,6-tetramethylpiperidine |
| TES | Triethylsilyl |
| TESCl | Triethylchlorosilane |
| TFA | Trifluoroacetic acid |
| THF | Tetrahydrofuran |
| TIPS | Triisopropylsiyl |
| TIPSCl | Triisopropylchlorosilane |
| TMS | Trimethylsilul |
| TMSCl | Trimethylchlorosilane |
| TPAP/NMO | Tetrapropylammonium Perruthenate/N-Methylmorpholine-N-Oxide |
| Ts | p-Toluene sulfonyl |
| XRPD | x-ray powder diffraction |

Reaction Schemes below illustrate the synthetic steps, reagents and conditions employed in the synthesis of the compounds described herein. The synthesis of compound I-7 which is the subject of this invention may be accomplished by one or more of similar routes.

EXAMPLE 1

Preparation of Compounds I-6 and I-7

Compounds I-6 and I-7 can be made from compound I-1 as described below in Scheme 1. NOTE: Compounds appearing within brackets [ ] denote non-isolated intermediates.

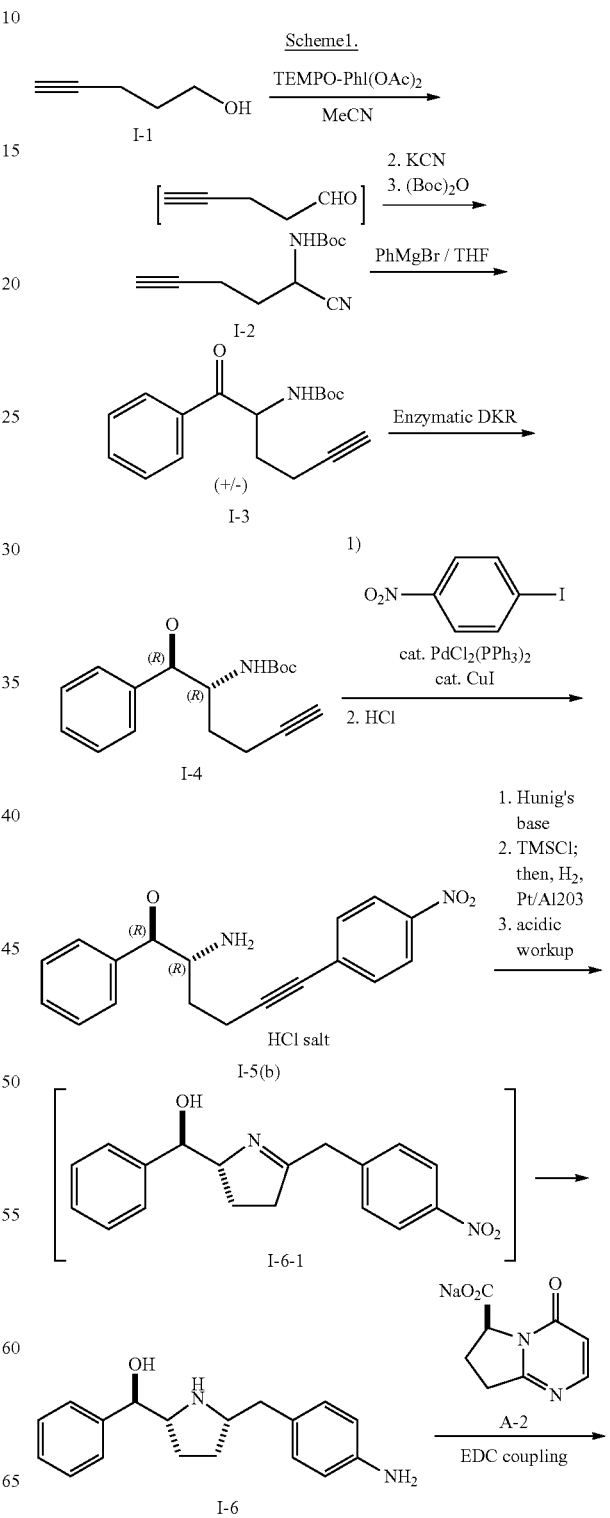

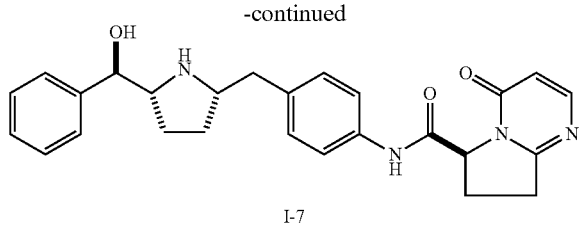

I-7

In Scheme 1, starting from 4-pentyn-1-ol (I-1), I-2 was prepared without isolating any intermediates via a TEMPO-PhI(OAc)$_2$ oxidation followed by a Strecker reaction (see Nitriles: General Methods and Aliphatic Nitriles. North, Michael. in Comprehensive Organic Functional Group Transformations, Volume 3, 1995, Pages 611-640, Editor(s): Katrizky, Alan R.; Meth-Cohn, Otto; Rees, Charles Wayne, Elsevier, Oxford, UK) and in situ Boc protection. Compound I-2 could be isolated as a solid. Treatment of I-2 with phenyl Grignard gave a racemic ketone I-3, which was then selectively transformed to optically pure alcohol I-4 under enzymatic (dynamic kinetic resolution) DKR reduction conditions, as the two stereogenic centers were set up in one step. I-5 was then prepared via a Sonogishira reaction followed by deprotection and isolated as a crystalline HCl salt. Treatment of I-5HCl salt with Hunig's base (Diisopropylethylamine; see Ketones: α,β-Unsaturated Ketones. Ebenezer, Warren J. and Wight, Paul. in Comprehensive Organic Functional Group Transformations, Volume 3, 1995, Pages 205-276, Editor(s): Katrizky, Alan R.; Meth-Cohn, Otto; Rees, Charles Wayne, Elsevier, Oxford, UK). In warm DMAc-THF gave cyclized intermediate I-6-1, which was further treated with TMSCl to protect the OH in situ. As such, a subsequent one-pot stereoselectively hydrogenated afforded the desired cis isomer in high yield. Finally, EDC coupling of I-6 and sodium salt of pyrimidinone acid A-2 completed the preparation of I-7. Detailed experimental conditions are described below.

Step 1. Preparation of Compound I-2 from Compound I-1

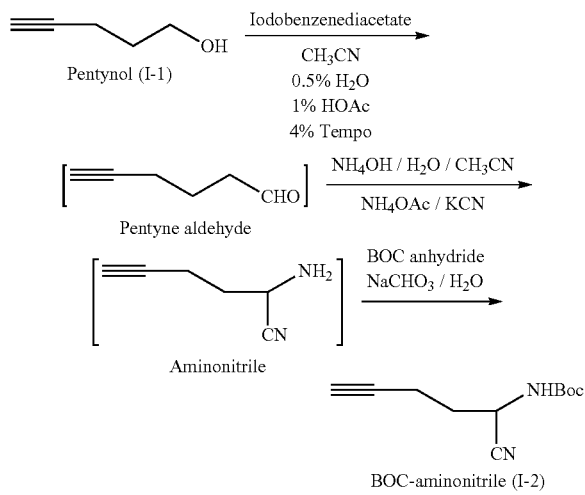

A 250 mL 3-neck round bottom flask equipped with an overhead stirrer was charged with 4-pentyn-1-ol (I-1) (10 g, 0.119 mol), acetonitrile (100 mL), water (0.5 mL), acetic acid (1.0 mL) and TEMPO (0.92 g, 5.8 mmol). Iodobenzene diacetate (39.4 g, 0.124 mol) was charged in portions over 2.5 hours, while the internal temperature was maintained at 20-25° C. with a cold water bath. The reaction was aged 3.5 hours at room temperature. The solution was used directly in subsequent Strecker reaction.

A 500 mL 3-neck round bottom flask equipped with an overhead stirrer was charged with water (40 mL), ammonium hydroxide (28 wt %, 40 mL), ammonium acetate (11.45 g, 0.149 mol) and potassium cyanide (9.68 g, 0.149 mol). After stirring to dissolve solids, the above crude aldehyde solution from the oxidation was added drop-wise while the internal temperature was maintained <40° C. The reaction was agitated at 45° C. for 7-10 hours. Acetonitrile was removed under reduced pressure while the internal temperature was maintained <25° C. EtOAc (200 mL) was added. The organic phase was separated.

Step 2. Crystallization of Compound I-2

To above crude organic solution was charged (BOC)$_2$O (26.0 g, 0.119 mol). The reaction mixture was gradually warmed to 35-40° C. and aged at 35-40° C. for additional 14 hours. The batch was cooled to ambient temperature and an aqueous solution of 7.5 wt % NaHCO$_3$ (50 mL). The separated organic layer was solvent switched to heptane at final volume of ~300 mL in vacuum, while the internal temperature was maintained at 35-45° C. The resulting slurry was aged 2 hours at 20° C. before filtration. The wet cake was washed with heptane (100 mL), and vacuum oven-dried at 40° C. to give 18.3 g of the product compound I-2. $^1$H NMR (400 MHz, CDCl$_3$): δ 5.09 (s, br, 1H), 4.74 (s, br, 1H), 2.43 (m, 2H), 2.08 (t, J=2.8 Hz, 1H), 2.04 (m, 2H), 1.47 (s, 9H).
$^{13}$C NMR (100 MHz, CDCl$_3$): δ 154.4, 118.5, 81.4, 70.9, 41.8, 32.1, 28.4, 15.1.

Alternative Crystallization Procedure for Compound I-2

The separated organic phase was concentrated to ~50 mL in vacuum, which was then added to a slurry of heptane (375 mL) seeded with product (125 mg) over several hours at 15-25° C. The batch was then solvent switched to heptane in vacuum at final volume of 250 mL, maintaining the internal temperature below 30° C. The resulting slurry was aged 2 hours at 20° C. before filtration. The wet cake was washed with heptane (100 mL), and vacuum oven-dried at 40° C. to give 18.3 g of the product Compound I-2.

Step 3. Preparation of Compound I-3 from Compound I-2

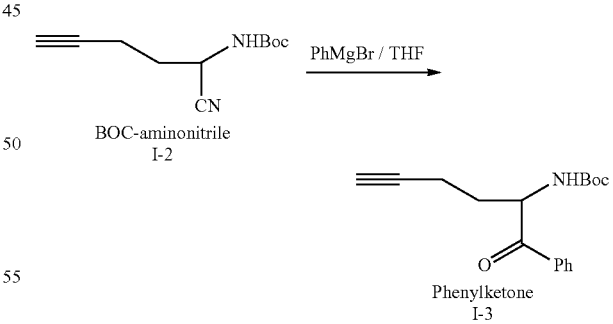

To a solution of PhMgBr (1Molar, "M", in THF, 106 mL, 0.106 mol) at −10° C. was added a solution of Boc aminonitrile I-2 (10 g, 0.048 mol) in THF (20 mL) dropwise over 2-3 hours. The reaction slurry was aged at 0° C. for additional 4 hours. The reaction mixture was then added to an aqueous solution of 10 wt % citric acid (135 mL) at −5° C. to 0° C. over 0.5 to 1 hour, maintaining the internal temperature below 20° C. The quenched biphasic solution was agitated at ambient temperature for 1 h and the layers were separated. The organic phase was washed with 10% brine (20 mL). The organic was azeotropically solvent-switched to isopropanol at a final volume of ~65 mL. The solution was heated to 35° C. and water (~25 mL) was added. The batch was seeded. After aging 30 minutes at 35° C., water (65 mL) was added dropwise over 1 hour. The slurry was aged an additional 30 minutes at 35° C., then, cooled to ambient temperature. The batch was agitated several hours before filtration. The wet cake was washed with 30% isopropanol in water (40 mL). Vacuum oven dry at 50° C. with nitrogen sweep gave Compound I-3. $^1$H NMR (400 MHz, CDCl$_3$): δ 8.02 (m, 2H), 7.61 (m, 1H), 7.50 (m, 2H), 5.47 (m, 1H), 5.42 (m, 1H), 2.37 (m, 1H), 2.27 (m, 1H), 2.15 (m, 1H), 2.01 (t, J=2.3 Hz, 1H), 1.75 (m, 1H), 1.46 (s, 9H).

$^{13}$C NMR (100 MHz, CDCl$_3$): δ 198.9, 155.8, 134.6, 134.1, 129.1, 129.0, 83.3, 80.2, 69.6, 54.5, 32.9, 28.6, 15.2.

Step 4. Preparation of Compound I-5 from Compound I-3

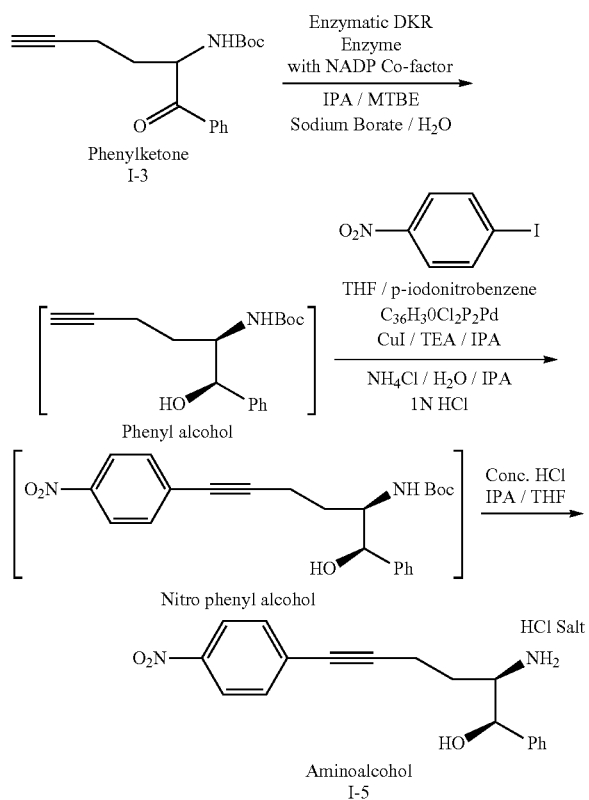

To a solution of sodium tetraborate decahydrate (18.7 g, 4.9 mmol) in water (1 L) at ambient temperature was added 5 Normal ("N") NaOH to pH of approximately 10. DKR enzyme (2 g) with the SEQ. ID. NO. 1 was added and dissolved with gentle agitation. A solution of beta-NADP-Na (0.2 g, 0.26 mmol) in water (20 mL) followed by a solution of phenyl ketone I-3 (100 g, 0.348 mol) in i-PrOH (1 L) was added at ambient temperature with good mixing. The batch was then agitated at 45° C. for at least 24 hours. The batch was cooled to ambient temperature and MTBE (1 L) was added. The separated aqueous phase was extracted with MTBE (0.5 L) and i-PrOH (0.5 L). The combined organic phase was washed with water (1 L). The separated organic phase was then azeotropically dried in vacuum at a final volume of ~0.3 L, maintaining the internal temperature below 45° C. The crude solution was directly used for next step. $^1$H NMR (400 MHz, CDCl$_3$): major rotomer: δ 7.34 (m, 4H), 7.28 (m, 1H), 4.75 (s, br, 1H), 4.73 (m, 1H), 3.82 (m, 1H), 3.27 (s, 1H), 2.27 (m, 2H), 1.97 (t, J=2.6 Hz, 1H), 1.83 (m, 1H), 1.72 (m, 1H), 1.37 (3, 9H). $^{13}$C NMR (100 MHz, d$_6$-DMSO): major rotomer: δ 156.7, 141.9, 128.5, 127.9, 126.5, 83.9, 79.9, 76.0, 69.1, 56.2, 30.6, 28.5, 15.7.

To crude solution was added THF (0.3 L) followed by p-iodonitrobenzene (90.4 g, 0.363 mol). After vacuum degass with nitrogen, bisotriphenylphosphine palladium (II) dichloride (2.43 g, 0.35 mmol) followed by CuI (1.3 g, 0.68 mmol) and triethyl amine (36.7 g, 0.363 mol) was added. The batch was agitated at ambient temperature for 3 h. i-PrOAc (1 L) was added. The batch was washed with 10% aq NH$_4$Cl (2×0.3 L) twice, 1 N HCl (0.3 L), and water (0.3 L). The separated organic phase was azeotropically solvent-switched to i-PrOH in vacuum to give a slurry at a final volume of ~0.6 L, maintaining the internal temperature below 45° C. Concentrated HCl (37%) was added and the batch was then agitated at 60° C. for 5 hours. The slurry was cooled to ambient temperature and aged for 3 hours before filtration. The wet cake was displacement washed with i-PrOH (0.2 L) followed by THF (2×0.2 L). The wet cake was then slurried in THF (0.76 L) at 60° C. for 4 hours. The slurry was filtered and displacement washed with THF (2×0.2 L). Vacuum oven drying at 40° C. with nitrogen sweep gave Compound I-5HCl salt. $^1$H NMR (500 MHz, CD$_3$OD): δ 8.19 (m, 2H), 7.55 (m, 2H), 7.47 (m, 2H), 7.41 (m, 2H), 7.36 (m, 1H), 4.71 (d, J=7.8 Hz, 1H), 2.54 (t, J=7.2 Hz, 2H), 1.88 (m, 2H).

$^{13}$C NMR (125 MHz, CD$_3$OD): δ 148.6, 142.0, 133.7, 131.6, 130.1, 129.9, 128.2, 124.7, 94.4, 81.5, 74.3, 57.9, 29.7, 16.8.

The crystalline HCl salt form of Compound I-5(b) can be characterized by XRPD by the following reflections with the d-spacing.

| Position [°2 Theta] | d-spacing [Å] |
| --- | --- |
| 4.2174 | 20.95196 |
| 8.5827 | 10.3028 |
| 12.9282 | 6.84784 |
| 13.5177 | 6.55051 |
| 16.65 | 5.32461 |
| 20.9425 | 4.24193 |
| 22.6974 | 3.91777 |
| 24.363 | 3.65356 |
| 24.6986 | 3.60468 |
| 28.1911 | 3.16555 |

Step 5. Preparation of Compound I-6 from Compound I-5(b)

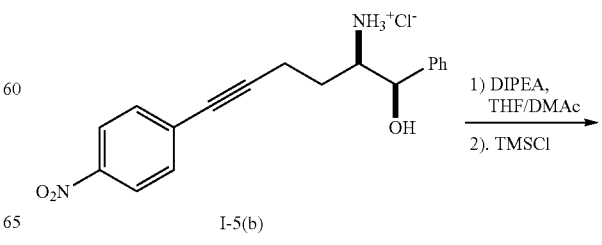

-continued

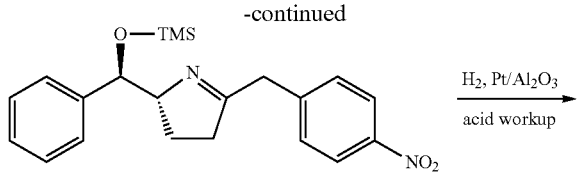

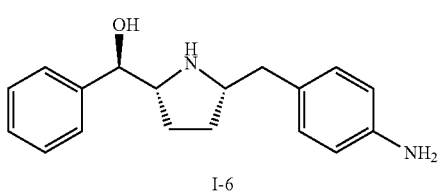
I-6

To a slurry of amino alcohol HCl salt (I-5(b)) (100 g, 0.288 mol) in THF (500 mL) and DMAc (100 mL) was added i-Pr₂NEt (151 mL, 0.87 mol) dropwise under nitrogen, while the internal temperature was maintained below 25° C. The batch was agitated at 55-65° C. for 3-5 hours, then cooled to 0-15° C. TMSCl (55.3 mL, 0.433 mol) was added dropwise over 1 hour, while the internal temperature was maintained between 0 and 15° C. After additional 0.5-1 hour, MeOH (35 mL, 0.87 mol) was added dropwise over 0.5 hour and the batch was aged for additional 0.5 hour. The reaction stream was then charged to a slurry of Pt/Al₂O₃ (5 wt %, 15 g) in THF (500 mL) at ambient temperature. The reaction mixture was hydrogenated at 50-100 psig of H₂ at 20° C. for 18 hours, followed by additional 6 hours at 50° C. Then, the catalyst was removed through filtration of a pad of SOLKA-FLOC® and washed with THF (400 mL). HCl (0.6 N, ~1.2 L) was added dropwise to pH=2, maintaining the batch temperature below 25° C. The batch was agitated at ambient temperature for 1 hour. Isopropyl acetate (300 mL) was added. The desired aqueous phase was separated and isopropyl acetate (400 mL) was added. Then, 5N NaOH (~30 mL) was added dropwise to adjust pH=10. The organic phase was separated and treated with active carbon (Cuno active carbon, 10 g) at ambient temperature for 1 hour. The carbon was removed through filtration and the filtrate was solvent switched to IPA at a volume of ~35 mL. The batch was warmed to 50° C. and water (30 mL) was added dropwise. Then, the batch was seeded at 42° C. and additional water (50 mL) was added dropwise over 2 hours. After addition, the batch was gradually cooled to 10° C. and aged additional several hours before filtration. The wet cake was washed with 25% IPA in water (50 mL). Suction drying gave the Compound I-6 hemihydrate.

¹H NMR (d₆-DMSO) δ 7.27 (m, 4H), 7.17 (m, 1H), 6.81 (d, J=8.1, 2H), 6.45 (d, J=8.1 Hz, 2H), 5.07 (s, br, 1H), 4.75 (s, 2H), 4.18 (d, J=7.0 Hz, 1H), 3.05 (m, 2H), 2.47 (dd, J=13.0, 6.7 Hz, 1H), 2.40 (dd, J=13.0, 6.6 Hz, 1H), 1.53 (m, 1H), 1.34 (m, 1H0, 1.22 (m, 2H).

¹³C NMR (d₆-DMSO) δ 146.5, 144.3, 129.2, 127.8, 127.4, 126.8, 126.7, 114.0, 76.8, 64.4, 60.1, 42.1, 30.2, 27.2.

Step 6a. Preparation of Compound A-2

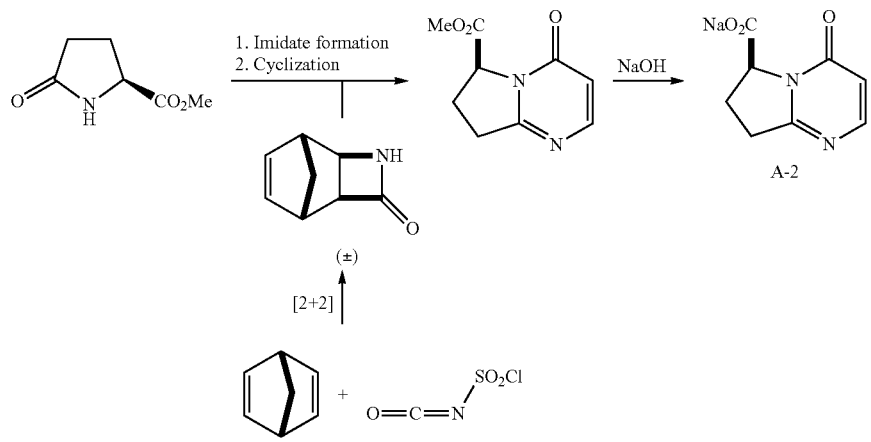

Step 6. Preparation of Compound I-7 from Compound I-6 and Compound A-2

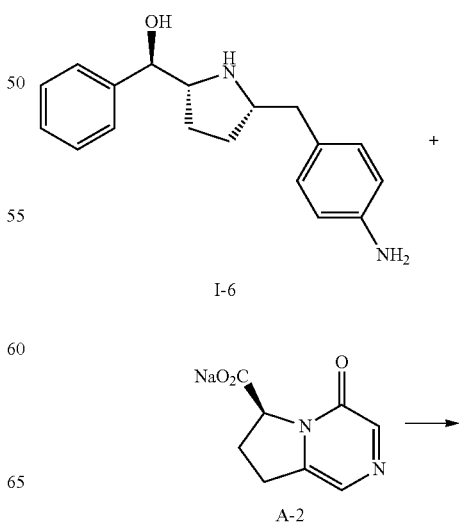

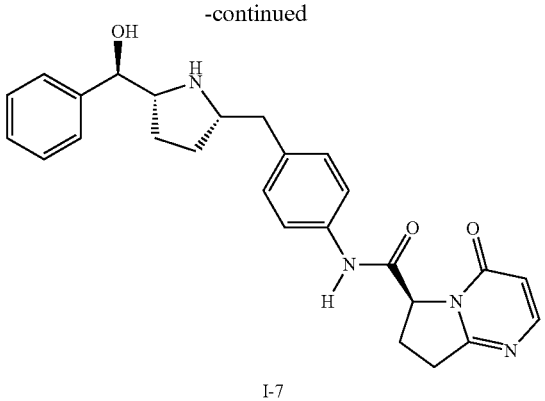

I-7

To a three neck flask equipped with a N$_2$ inlet, a thermo couple probe was charged pyrrolidine hemihydrate I-6 (10.3 g), sodium salt A-2 (7.87 g), followed by IPA (40 mL) and water (24 mL). 5 N HCl (14.9 mL) was then slowly added over a period of 20 minutes to adjust pH=3.3-3.5, maintaining the batch temperature below 35° C. Solid EDC hydrochloride (7.47 g) was charged in portions over 30 minutes. The reaction mixture was aged at RT for additional 0.5-1 hour, aqueous ammonia (14%) was added dropwise to pH ~8.6. The batch was seeded and aged for additional 1 hour to form a slurry bed. The rest aqueous ammonia (14%, 53.2 ml total) was added dropwise over 6 hours. The resulting thick slurry was aged 2-3 hours before filtration. The wet-cake was displacement washed with 30% IPA (30 mL), followed by 15% IPA (2×20 mL) and water (2×20 mL). The cake was suction dried under N$_2$ overnight to afford 14.3 g of compound I-7.

$^1$H NMR (DMSO) δ 10.40 (s, NH), 7.92 (d, J=6.8, 1H), 7.50 (m, 2H), 7.32 (m, 2H), 7.29 (m, 2H), 7.21 (m, 1H), 7.16 (m, 2H), 6.24 (d, J=6.8, 1H), 5.13 (dd, J=9.6, 3.1, 1H), 5.08 (br s, OH), 4.22 (d, J=7.2, 1H), 3.19 (p, J=7.0, 1H), 3.16-3.01 (m, 3H), 2.65 (m, 1H), 2.59-2.49 (m, 2H), 2.45 (br s, NH), 2.16 (ddt, J=13.0, 9.6, 3.1, 1H), 1.58 (m, 1H), 1.39 (m, 1H), 1.31-1.24 (m, 2H).

$^{13}$C NMR (DMSO) δ 167.52, 165.85, 159.83, 154.56, 144.19, 136.48, 135.66, 129.16, 127.71, 126.78, 126.62, 119.07, 112.00, 76.71, 64.34, 61.05, 59.60, 42.22, 31.26, 30.12, 27.09, 23.82.

The crystalline freebase anhydrous form I of Compound I-7 can be characterized by XRPD by the following reflections with the d-spacing.

| Position [°2 Theta] | d-spacing [Å] |
|---|---|
| 5.4897 | 16.09873 |
| 8.7494 | 10.10683 |
| 11.0426 | 8.01261 |
| 16.4521 | 5.38818 |
| 16.6518 | 5.32402 |
| 17.4975 | 5.06857 |
| 18.853 | 4.7071 |
| 21.2176 | 4.18756 |
| 21.7532 | 4.08564 |
| 22.7425 | 3.9101 |

EXAMPLE 2

Preparation of Compound I-7 from Compound I-6

To a three neck flask equipped with a N$_2$ inlet, a thermo couple probe was charged pyrrolidine hemihydrate I-6 (10.3 g), sodium salt A-2 (7.5 g), followed by IPA (40 mL), pyridine (0.42 mL), and water (21 mL). 5 N HCl (14.9 mL) was then slowly added over a period of 20 minutes to adjust pH=3.1-3.7, maintaining the batch temperature below 25° C. The batch was cooled to 5-10° C. Solid EDC hydrochloride (7.5 g) was charged in portions over 30 min to 1 hour, maintain the batch temperature below 15° C. The reaction mixture was then aged between 5-10° C. for additional 0.5-1 hour. IPA (8 mL) and water (7 mL) were added at rt. Aqueous ammonia (10%, ~3.5 mL) was added dropwise to pH ~7.9. The batch was seeded and aged for additional 1 hour to form a slurry bed. More aqueous ammonia (10%, 32 mL) was added dropwise over 6-10 hours. The resulting thick slurry was aged 2-3 h before filtration. The wet-cake was displacement washed with 30% IPA (30 mL), followed by 15% IPA (2×20 mL) and water (2×20 mL). The cake was suction dried under N$_2$ overnight to afford 14.3 g of compound I-7.

EXAMPLE 3

Immobilization of KRED Enzyme:

To a solution of sodium potassium phosphate (6.097 g, 3.5 mmol) in water (35 mL) at ambient temperature was added KRED enzyme (875 mg) and NADP (70 mg) and were dissolved with gentle agitation. Polymethacrylic resin, DIAION™ HP2MG, (MITSUBISHI CHEMICALS) (10 g) was added. The mixture was gently agitated at 25° C. for at least 16 hours. The resin was drained of all solution. The wet resin was washed with a solution of potassium dibasic phosphate and subsequently drained. The wet resin was stored at 4° C.

Ketone Reduction Procedure:

Immobilized KRED enzyme (120 mg) was added to a solution of ketone (50 mg) dissolved in 90% IPA 10% water mixture containing immobilized carbonate (50 mg). The mixture was agitated at 25° C. for at least 24 hours. The batch was filtered and concentrated.

EXAMPLE 4

Immobilization of KRED Enzyme with Resin Immobead™ 150A (IB-150A):

To a solution of 0.1M sodium potassium phosphate at pH 7.0 (20 mL) at ambient temperature was added KRED enzyme with the SEQ. ID. NO. 1 (2 g) and dissolved with gentle agitation. Resin IB-150A (10 g) (commercially available from ChiralVision™, The Netherlands) was charged and aged at 25° C. for 24-48 hours. The resin was filtered off all solution, and washed three times with 0.1 M solution of sodium potassium phosphate at pH 7 and dried. The resin was stored at 4° C. for use.

Ketone Reduction to Preparation of Phenyl Alcohol by Immobilized KRED Enzyme:

To a 1 L flask was charged 360 ml IPA and 40 ml water, followed by ketone I-3 (21 g, 73.1 mmol) and 1,4-diazabicyclooctane (41.0 g, 365 mmol) at 25° C. The mixture was agitated until all was dissolved. Immobilized SEQ ID NO. 1 (10.5 g, 50 wt %) was charged to flask and the reaction mixture was heated to 50° C. with gentle agitation. Upon aging for about 28 hours the reaction typically gave 98% conversion, 99% ee and 100:1 Dr. The reaction was cooled to 25° C. and filtered to remove immobilized SEQ ID NO. 1 and rinsed with 100 ml (5 vol) IPA. The recovered immobilized SEQ ID NO. 1 can be charged to fresh solution of ketone/DABCO IPA/water solution, and recycled up to 9 rounds while reaching specifications for conversion and selectivity. After removing immobilized enzyme the crude reaction solution was azeotropically dried to remove water and reduce reaction volume to ~5 volumes IPA. Phosphoric acid (5 eq, 1:1 ratio with DABCO) was added at 25° C. and subsequent slurry was aged for 4 hours. The slurry was filtered to remove at least 96% of DABCO salt from solution. Crude solution of phenyl alcohol was directly used in subsequent step.

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

```
SEQ ID NO. 1:
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Ala Arg Leu Gly Ile Gln Arg
            115                 120                 125

Met Lys Asn Lys Gly Leu Gly Ala Ser Ile Ile Asn Met Ser Ser Val
        130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Ser Tyr Glu Gly Ala Glu Glu Met Phe Ser Gln
            195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

What is claimed is:

1. A process of making compound I-6:

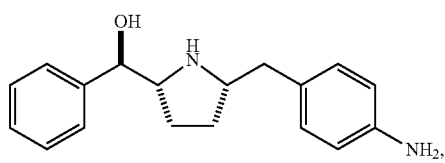

I-6 comprising:

(a-2) reducing compound I-3:

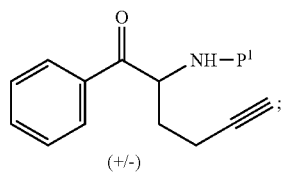

I-3 in the presence of a ketoreductase (KRED) enzyme to produce compound I-4:

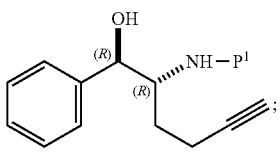

I-4

(b-2) coupling compound I-4 with compound A-1, in the presence of Catalyst D to produce compound I-5(a):

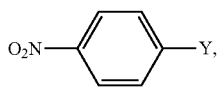

A-1 followed by deprotecting in situ with an acid to produce compound I-5(b) as a salt:

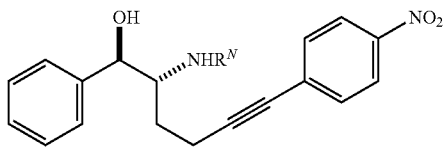

I-5(a), where $R^N=P^1$ or I-5 (b), where $R^N$=H I-5(a), where $R^N=P^1$ or I-5(b) where, $R^N$=H; and (c-2) cyclizing and reducing compound I-5(b) in the presence of Catalyst E to produce compound I-6 via I-6-1:

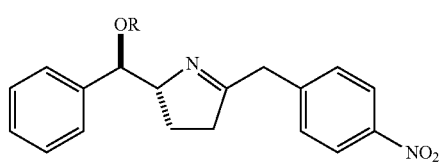

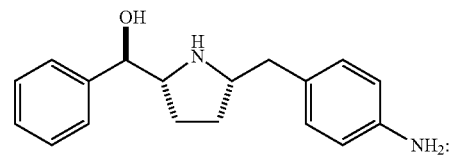

wherein $P^1$ is selected from the group consisting of Ac, Bn, Boc, Bz, Cbz, DMPM, FMOC, Ns, Moz, and Ts; and Y is selected from the group consisting of Cl, I, Br, and OTf; and R is selected from the group consisting of H, TMS, TES, TBDMS, TIPS and TBDPS; and $R^N$ is $P^1$ or H.

2. A process of making compound I-7:

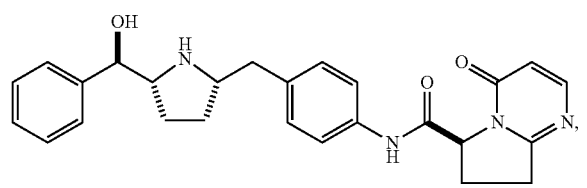

comprising:
(a-2) reducing compound I-3;

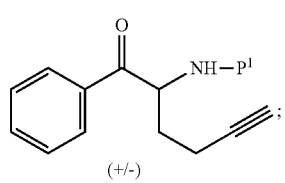

in the presence of a KRED enzyme to produce compound I-4:

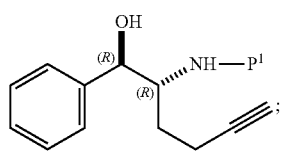

(b-2) coupling compound I-4 with compound A-1, in the presence of Catalyst D to produce compound I-5(a):

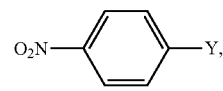

followed by deprotecting in situ with an acid to produce compound I-5(b) as a salt:

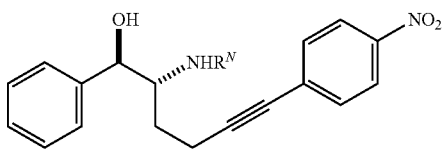

I-5(a), where $R^N=P^1$ or I-5 (b) where, $R^N$=H I-5(a), where $R^N=P^1$ or I-5(b) where, $R^N$=H;

(c-2) cyclizing and reducing compound I-5(b) in the presence of Catalyst E to produce compound I-6 via I-6-1:

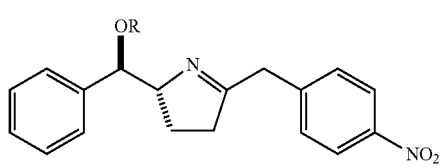

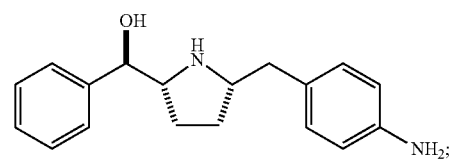

and (d-2) coupling compound I-6 with compound A-2:

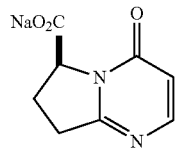

in the presence of a coupling agent and optionally including a base to produce compound I-7;

I-7

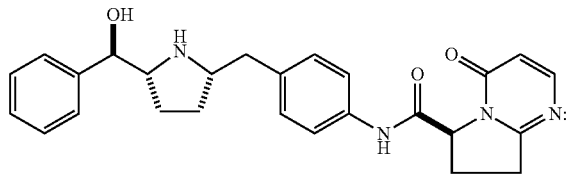

wherein P¹ is selected from the group consisting of Ac, Bn, Boc, Bz, Cbz, DMPM, FMOC, Ns, Moz, and Ts; and Y is selected from the group consisting of Cl, I, Br, and OTf; and R is selected from the group consisting of H, TMS, TES, TBDMS, TIPS and TBDPS; and R^N is P¹ or H.

3. A process of making compound I-6:

I-6

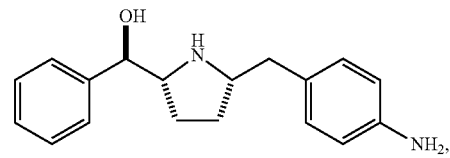

comprising:

(a-1) reacting compound I-1:

I-1

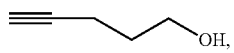

in the presence of a solvent, an oxidizing agent, and Catalyst A to form an aldehyde in situ, followed by a condensation in the presence of NaCN or KCN and ammonium chloride and a protective reagent to produce compound I-2:

I-2

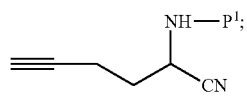

(b-1) reacting compound I-2 in the presence of a phenyl Grignard reagent to produce compound I-3:

I-3

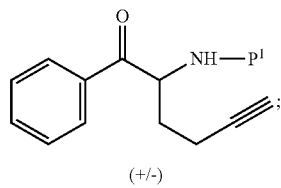

(c-1) reducing compound I-3 in the presence of a KRED enzyme to produce compound I-4:

I-4

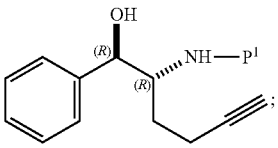

(d-1) coupling compound I-4 with compound A-1, in the presence of Catalyst D to produce compound I-5(a):

A-1

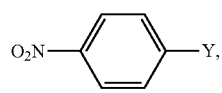

followed by deprotecting in situ with an acid to produce compound I-5(b) as a salt:

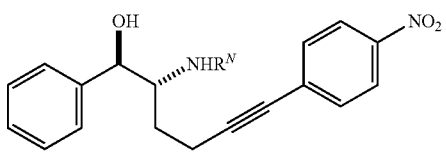

I-5(a), where R^N=P¹ or I-5 (b) where, R^N=H I-5(a), where R^N=P¹ or I-5(b) where, R^N=H; and (e-1) cyclizing and reducing compound I-5(b) in the presence of Catalyst E to produce compound I-6 via I-6-1:

I-6-1

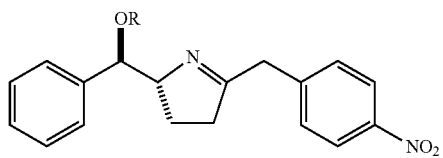

I-6

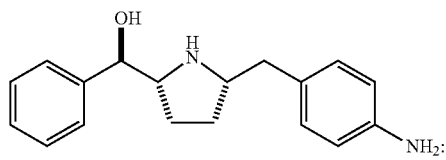

wherein P¹ is selected from the group consisting of Ac, Bn, Boc, Bz, Cbz, DMPM, FMOC, Ns, Moz, and Ts; and Y is selected from the group consisting of Cl, I, Br, and OTT; and R is selected from the group consisting of H, TMS, TES, TBDMS, TIPS and TBDPS;

and R^N is P¹ or H.

4. The process of claim 3, wherein in step (a-1): the solvent is selected from the group consisting of THF, MTBE, CH₂Cl₂, MeCN, EtOAc, i-PrOAc, Me-THF, hexane, heptane, DMAc, DMF, methyl cyclopentyl ether, toluene and combinations thereof; the oxidizing agent is selected from the group consisting of NaOCl, NaClO₂, PhI(OAc)₂, hydrogen peroxide; pyridine sulfur trioxide/

Et₃N/DMSO and a Moffatt variant, PCC, DCC, a Swern oxidation or its variants, and TPAP/NMO; and Catalyst A is TEMPO or a TEMPO analogue.

5. The process of claim 3, wherein P¹ in step (a-1) is Boc.

6. The process of claim 3, wherein step (a-1) is carried out at a temperature of about 35° C.' to about 45° C. in the presence of EtOAc or i-PrOAc.

7. The process of claim 3, wherein in step (a-1) compound I-2 can be prepared via a hydrogensulfite adduct.

8. The process of claim 2, wherein the KRED enzyme in step (a-2) comprises the amino acid sequence set forth in SEQ NO.1 or an active fragment thereof.

9. The process of claim 2, wherein a cofactor recycling system is present in step (a-2).

10. The process of claim 2, wherein the reaction in step (a-2) is carried out in a solvent selected from the group consisting of 2-propanol, sec-butanol, iso-butanol, DMSO, DMF, DMAc, NMP, and combinations thereof.

11. The process of claim 2, wherein the reaction in step is carried out in a pH range of above about 8.

12. The process of claim 2, wherein the reaction in step (a-2) is carried out at a temperature of about 30° C. to about 50° C.

13. The process of claim 2, wherein Catalyst D used in the reaction in step (b-2) is selected from the group consisting of Pd(PPh₃)₄, PdCl₂, (PPh₃)₂PdCl₂, Pd(dppe)Cl, Pd(dppp)Cl₂, Pd(dppf)Cl₂, and Pd(OAc)₂/Ph₃P, in the presence or absence of a catalytic amount of material selected from the group consisting of CuI, CuBr, and CuCl.

14. The process of claim 2, wherein the reaction in step (b-2) is carried out in the presence of a solvent selected from the group consisting of THF, IPA, MeOH, EtOH, n-PrOH, NMP, DMF, DMAc, MTBE, CH₂Cl₂, MeCN, Me-THF, methyl cyclopentyl ether, toluene, and combinations thereof.

15. The process of claim 2, wherein the reaction product in step (b-2) is isolated as a solid HCl salt.

16. The process of claim 2, wherein compound I-5(b) salt reacts in step (c-2) with a base selected from the group consisting of Et₃N, i-Pr₂NEt, i-Pr₂NH, pyridine, lutidine, N-methyl morphine, t-BuOK, t-BuONa, t-BuOLi, NaH, NaHMDS, LiHMDS, and KHMDS to produce compound I-6-1 through an intramolecular cyclization reaction.

17. The process of claim 2, wherein compound I-6-1 is reduced to compound I-6 in step (c-2) in the presence of hydrogen gas and Catalyst E.

18. The process of claim 3, wherein the reaction product in step (d-1) is isolated as a solid HCl salt.

19. A process of making compound I-6:

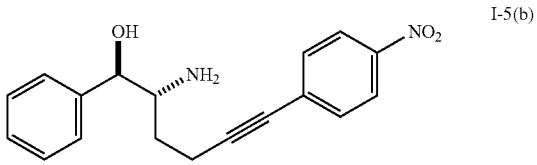

comprising:
(c-2) cyclizing and reducing compound I-5(b) or a salt thereof:

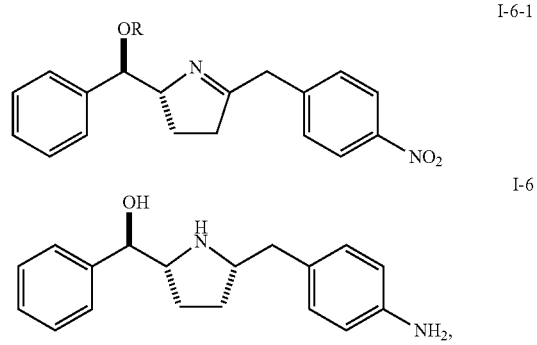

in the presence of Catalyst E to produce compound I-6 via I-6-1:

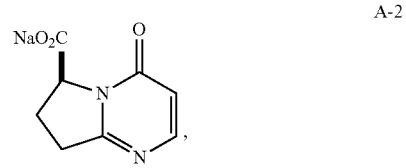

wherein R is selected from the group consisting of H, TMS, TES, TBDMS, TIPS and TBDPS.

20. The process of claim 19, further comprising:
(d-2) coupling compound I-6 with compound A-2:

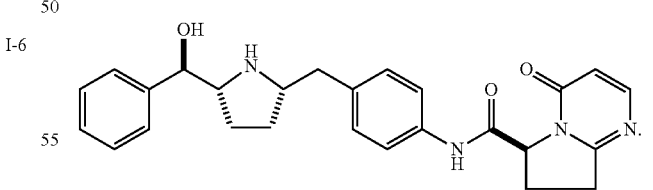

in the presence of a coupling agent and optionally including a base to produce compound I-7:

* * * * *

UNITED STATES PATENT AND TRADEMARK OFFICE
CERTIFICATE OF CORRECTION

PATENT NO. : 10,287,289 B2
APPLICATION NO. : 14/776366
DATED : May 14, 2019
INVENTOR(S) : Xu et al.

It is certified that error appears in the above-identified patent and that said Letters Patent is hereby corrected as shown below:

In the Specification

In Column 2, Line 45, delete "I-5(a)" and insert -- I-5(a): --, therefor.

In Column 4, Line 12, delete "I-5(a)" and insert -- I-5(a): --, therefor.

In Column 6, Line 24, delete "I-5(a)" and insert -- I-5(a): --, therefor.

In Column 8, Line 11, delete "a2)," and insert -- a-2), --, therefor.

In Column 8, Line 28, delete "Sonogoshira" and insert -- Sonogashira --, therefor.

In Column 8, Line 32, delete "Sonogoshira," and insert -- Sonogashira, --, therefor.

In Column 8, Line 36, delete "Sonogoshira" and insert -- Sonogashira --, therefor.

In Column 9, Lines 6-10, delete "  ", therefor.

In Column 10, Line 54, delete "deydrogenase" and insert -- dehydrogenase --, therefor.

In Column 12, Line 58, delete "Dicyclohexycarbodiimide" and insert -- Dicyclohexylcarbodiimide --, therefor.

In Column 13, Line 38, delete "phospate Paladium" and insert -- phosphate Palladium --, therefor.

In Column 13, Line 54, delete "Triisopropylsiyl" and insert -- Triisopropylsilyl --, therefor.

In Column 13, Line 56, delete "Trimethylsilul" and insert -- Trimethylsilyl --, therefor.

Signed and Sealed this
Third Day of September, 2019

Andrei Iancu
*Director of the United States Patent and Trademark Office*

CERTIFICATE OF CORRECTION (continued)
U.S. Pat. No. 10,287,289 B2

In Column 14, Lines 33-35, delete "  " and insert -- -- , therefor.

In Column 14, Lines 43-45, delete " 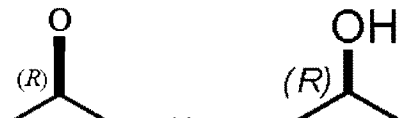 " and insert -- -- , therefor.

In Column 15, Line 25, delete "Sonogishira" and insert -- Sonogashira --, therefor.

In Column 22, Line 64, delete "vol)" and insert -- vol.) --, therefor.

In the Claims

In Column 27, Claim 1, Lines 9-10, delete
"I-5(a), where $R^N=P^1$ or I-5 (b), where $R^N=H$ I-5(a), where $R^N=P^1$ or I-5(b) where, $R^N=H$; and" and insert
-- I-5(a), where $R^N=P^1$ or I-5(b), where $R^N=H$; and --, therefor.

In Column 27, Claim 2, Line 54, delete "I-3;" and insert -- I-3: --, therefor.

In Column 28, Claim 2, Lines 31-32, delete
"I-5(a), where $R^N=P^1$ or I-5 (b), where, $R^N=H$ I-5(a), where $R^N=P^1$ or I-5(b) where, $R^N=H$;" and insert
-- I-5(a), where $R^N=P^1$ or I-5(b), where $R^N=H$; --, therefor.

In Column 30, Claim 3, Lines 31-32, delete
"I-5(a), where $R^N=P^1$ or I-5 (b), where, $R^N=H$ I-5(a), where $R^N=P^1$ or I-5(b) where, $R^N=H$; and" and insert
-- I-5(a), where $R^N=P^1$ or I-5(b), where $R^N=H$; and --, therefor.

In Column 30, Claim 3, Line 57, delete "OTT;" and insert -- OTf; --, therefor.

In Column 31, Claim 6, Line 6, delete "35° C.'" and insert -- 35° C. --, therefor.

In Column 31, Claim 8, Line 13, delete "SEQ" and insert -- SEQ ID --, therefor.

In Column 31, Claim 11, Line 20, delete "step" and insert -- step (a-2) --, therefor.

SEQUENCE LISTING

<160> NUMBER OF SEQ ID NOS: 1

<210> SEQ ID NO 1
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 1

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala

-continued

```
                20                  25                  30
Lys Val Val Ile Thr Gly Arg Arg Ala Asp Val Gly Glu Lys Ala Ala
            35                  40                  45
Lys Ser Ile Gly Gly Thr Asp Val Ile Arg Phe Val Gln His Asp Val
        50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Met Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Ala Arg Leu Gly Ile Gln Arg
        115                 120                 125
Met Lys Asn Lys Gly Leu Gly Ala Ser Ile Ile Asn Met Ser Ser Val
        130                 135                 140
Phe Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Ser Tyr Glu Gly Ala Glu Met Phe Ser Gln
            195                 200                 205
Arg Thr Lys Thr Pro Met Gly His Ile Gly Glu Pro Asn Asp Ile Ala
        210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Phe Thr Ala Gln
            245                 250
```